United States Patent [19]

Becker et al.

[11] Patent Number: 5,237,113
[45] Date of Patent: Aug. 17, 1993

[54] PREPARATION OF HALOALCOHOLS

[75] Inventors: Rainer Becker; Wolfgang Mackenroth, both of Bad Duerkheim; Walter Seufert, Spever, all of Fed. Rep. of Germany

[73] Assignee: BASF Altiengesellschaft, Ludwigshafen, Fed. Rep. of Germany

[21] Appl. No.: 973,553

[22] Filed: Nov. 9, 1992

Related U.S. Application Data

[63] Continuation of Ser. No. 908,935, Jul. 6, 1992, abandoned, which is a continuation of Ser. No. 665,916, Mar. 4, 1991, abandoned, which is a continuation of Ser. No. 488,530, Feb. 28, 1990, abandoned, which is a continuation of Ser. No. 401,530, Aug. 30, 1989, abandoned, which is a continuation of Ser. No. 277,455, Nov. 23, 1988, abandoned, which is a continuation of Ser. No. 102,862, Sep. 30, 1987, abandoned.

[51] Int. Cl.$^5$ .............................. C07C 29/62
[52] U.S. Cl. ........................ 568/841; 568/678; 568/619; 568/55; 564/478
[58] Field of Search ............. 568/841, 842, 678, 619, 568/55; 564/428

[56] References Cited

FOREIGN PATENT DOCUMENTS 130943 8/1982 Japan.

OTHER PUBLICATIONS

Campbell et al, Org. Syn., Coll vol. III (1955) pp. 446–448.
Camps et al, Org Prep and Proc. Int., 15 (1983) pp. 63–70.
J. Chem. Soc. (1931), 1697 ff.
J. Chem. Soc. (1938), 813–815.
J. Amer. Chem. Soc (1950), 72, 5137–5139.
Org. Prep. and Proc., int. 15 (1983), 63–70.

Primary Examiner—Howard T. Mars
Attorney, Agent, or Firm—John H. Shurtleff

[57] ABSTRACT

Haloalcohols of the general formula I $$Hal-X-OH \qquad (I)$$

where X is straight-chain or branched, substituted or unsubstituted alkylene of 4 or more carbon atoms in the chain, which may be interrupted by one or more heteroatoms, and Hal is halogen, are prepared by reacting a diol of the general formula II $$HO-X-OH \qquad (II)$$

where X has the above meanings, with an aqueous hydrogen halide solution in a water-immiscible organic solvent which is inert under the reaction conditions, at from 50° to 150° C., using an excess of hydrogen halide, based on the diol of the general formula II, of from 10 to 200 mole percent and setting a volume ratio of inorganic phase: organic phase of from 1:2 to 1:50.

10 Claims, No Drawings

PREPARATION OF HALOALCOHOLS

This application is a continuation of application Ser. No. 07/908,935, filed Jul. 6, 1992, which is a continuation of application Ser. No. 665,916, filed Mar. 4, 1991, which is a continuation of Ser. No. 488,530, filed Feb. 28, 1990, which is a continuation of Ser. No. 401,530, filed Aug. 30, 1989, which is a continuation of Ser. No. 277,455, filed Nov. 23, 1988, which is a continuation of Ser. No. 102,862, all now abandoned, filed Sep. 30, 1987.

The present invention relates to a process for preparing a haloalcohol from a diol.

It is known that one of the products of reacting a long-chain diprimary diol with a halohydric acid is the monohaloalcohol. For instance, according to Monatsh. Chem. 27 (1906), 411 the action of concentrated hydrochloric acid on decane-1,10-diol produces chlorodecanol in an approximately 50% yield. However, reproducing this result proved difficult, especially because of problems with the purification, so that J. Chem. Soc. (1931), 1697-1701 proposed a process involving an expensive continuous extraction to permanently withdraw the desired product, chlorodecanol, from the reaction mixture, thereby to avoid further reaction to dichlorodecane or dimeric products. This reference provides no information on the chlorodecanol yield. Applying the process to chloroheptanol produces the product in a 43% yield. It is true that in the case of chlorooctanol the yield is 80%, but the product is contaminated with impurities which cannot be separated off. The process was also used to prepare chlorononanol, but again no yield is given. J. Chem. Soc. (1938), 813-815 describes the preparation of chlorohexanol by the above method with continuous extraction, but again without stating the yield.

A detailed study of the reaction of hexanediol with hydrogen chloride is described in Monatsh. Chem. 77 (1947), 259-263. Here in turn, the complicated continuous extraction was dispensed with, and dry hydrogen chloride was passed in. Depending on the specific conditions, chlorohexanol is formed in a maximum yield of 45%; byproducts are, inter alia, dichlorohexane in a maximum yield of 35% and also dichlorodihexyl ether, chlorohydroxydihexyl ether and dihydroxydihexyl ether. The analogous reaction of hexanediol with gaseous HBr is described in Ber. dtsch. chem. Ges. 77 (1944), 669-675, and leads to a predominant amount of dibromohexane with virtually no bromohexanol. The synthesis of bromohexanol, this time again with the aid of the continuous extraction, is described in J. Amer. Chem. Soc. 72 (1950), 5137-5139. A systematic study of the formation of bromoalcohols by reaction of diols with HBr and continuous extraction of the reaction mixture is described in Org. prep. and proc. int. 15 (1983), 63-70. Yields between 60 and 85% are obtained with a 2 to 8% dihalide content and a 3- to 12-fold HBr excess. The references therein to alleged preparations on a large scale relates to continuous extractions involving less than 50 g of substance. Indeed, scaling up this laboratory-tested method to industrial requirements presents considerable problems with the hardware, since, on the one hand, expensive special extraction kettles are required for the reaction and, on the other, very large solvent quantities or an additional continuous solvent recycle loop are necessary. In the latter case, the continuous withdrawing and recycling of the solvent in a separate kettle leads to an increase in the concentration of small HHal quantities which are carried over in the extraction and lead to secondary reactions (dihalide or ether formation) and thus to an inferior product. Communications 1985, 1161-1163 describes a simplified bromoalcohol synthesis involving continuous removal of water from the reaction mixture by distillation. However, when these experiments are repeated, the claimed results are not confirmed; in the case of the conversion of butanediol to bromobutanol the yield obtained is only between 50 and 60% (literature claim 65%) and the dibromide content between 2.5 and 6% (literature claim 0%), depending on the rate of water removal (which depends on the bath temperature). Here too scaleup for industry is expensive and complicated on account of the water removal required.

The haloalcohols obtainable according to the invention are useful intermediates and are utilizable in numerous syntheses, in particular those of active substances.

It is an object of the present invention to develop a process for preparing a haloalcohol of the formula Hal—x—OH (I) where X is a straight-chain or branched, substituted or unsubstituted alkylene of 4 or more carbon atoms in the chain which may be interrupted by one or more heteroatoms, and Hal is halogen, the process being carried out in such a way that it permits the preparation of a haloalcohol on an industrial scale in good yield and high selectivity.

We have found that this object is achieved with a process for preparing a haloalcohol of the general formula I

$$\text{Hal—X—OH} \qquad (I)$$

where X is straight-chain or branched, substituted or unsubstituted alkylene of 4 or more carbon atoms in the chain, which may be interrupted by one or more heteroatoms, and Hal is halogen (fluorine, chlorine, bromine or iodine), which comprises reacting a diol of the general formula II

$$\text{HO—X—OH} \qquad (II)$$

where X has the above meanings, with an aqueous hydrogen halide solution in a water-immiscible organic solvent which is inert under the reaction conditions, at from 50° to 150° C., using an excess of hydrogen halide, based on the diol of the general formula II, of from 10 to 200 mole percent and setting a volume ratio of inorganic phase: organic phase of from 1:2 to 1:50 and the reaction being carried out without a continuous phase separation either by continuous extraction or by continuous distillation, for removal of any components of the reaction system.

In a preferred embodiment of the process according to the invention, X is straight-chain or branched alkylene of 4 to 12 carbon atoms. Particularly advantageously, X is straight-chain alkylene of 4 to 12 carbon atoms. It is advantageous to use aqueous hydrogen chloride or hydrogen bromide solution. If a hydrogen chloride solution is used, the concentration thereof advantageously ranges from 18 to 36% by weight. If an aqueous hydrogen bromide solution is used, the concentration thereof advantageously ranges from 24 to 48% by weight.

The organic solvent used is preferably a hydrocarbon solvent, in particular an alkane, cycloalkane, aromatic, haloalkane or haloaromatic. Particularly suitable representatives are hexane, heptane, octane or mixtures thereof, cyclohexane, benzene, toluene, the isomeric xylenes (o-, m- and p-xylene) or chlorobenzenes, for example monochlorobenzene or dichlorobenzene. It is essential that the organic solvent not be miscible with water and not react with the halohydric acid. It is also possible to use a commercially available hydrocarbon mixture, for example one of those obtainable under the trade name Skellysolve ®.

In the process according to the invention, the volume ratio of inorganic phase:organic phase is chosen to range from 1:2 to 1:50, preferably from 1:5 to 1:15.

The reaction temperature of the process according to the invention ranges from 50° to 150° C., preferably from 90° to 120° C.

The hydrogen halide is used in an excess which, based on the diol used, ranges from 10 to 200 mol %, preferably from 20 to 50 mol %.

Using the process according to the invention, it is surprisingly possible to prepare a haloalcohol in a conventional kettle by reaction of a diol with an aqueous halohydric acid in good yield and high selectivity without the need for a continuous phase separation (extraction or distillation).

It is important with the process according to the invention to ensure thorough mixing of the two-phase system, and this can be effected in a conventional manner, for example by stirring or some other form of agitation.

In the compound of the general formula I, X can be straight-chain or branched, substituted or unsubstituted alkylene of 4 or more carbon atoms, in particular of 4 to 12 carbon atoms, in the chain. This alkylene may be interrupted by one or more, in particular 1 or 2, heteroatoms, for example oxygen, sulfur or nitrogen atoms. Examples of heteroatom-interrupted alkylene chains are: $-(CH_2)_2-O-(CH_2)_2-$, $-(CH_2)_3-O-(CH_2)_3-$, $-(CH_2)_4-O-(CH_2)_4-$, $-(CH_2)_2-O-(CH_2)_2-O-(CH_2)_2-$, $-(CH_2)_2-O-(CH_2)_3-$, $-(CH_2)_2-NH-(CH_2)_2-$, $-(CH_2)_3-N(CH_3)-(CH_2)_3-$, $-(CH_2)_3-S-(CH_2)_3-$. The preferred heteroatom is oxygen. In the case of nitrogen as the heteroatom, the nitrogen is additionally substituted by hydrogen or alkyl, in particular $C_1-C_4$-alkyl. If the alkylene is substituted, the substituent will be of a type which does not react with the hydrogen halide under the reaction conditions. Examples of substituents of this type are: alkyls such as methyl, ethyl, propyl, butyl, isopropyl, sec-butyl, isobutyl, phenyl, substituted phenyl, alkoxy and carboxyl.

Particularly preferred starting diols of the general formula II are 1,4-butanediol, 1-5-pentanediol, 1,6-hexanediol, 1,7-heptanediol, 1,8-octanediol, 1,9-nonanediol, 1,10-decanediol, 1,11-undecanediol and 1,12-dodecanediol. The diols of the general formula II are either known or obtainable in a conventional manner.

The invention is illustrated in more detail by the Examples which follow.

EXAMPLE 1

Preparation of 8-bromoctan-1-ol

In a 6 m³ kettle, 235 kg of octane-1,8-diol were stirred under reflux with 3 m³ of toluene and 440 kg of HBr (48% strength) for 40 hours. The aqueous phase was then separated off. The toluene phase was thoroughly washed with 500 l of water, then with 500 l of 10% strength sodium carbonate solution and then again with 500 l of water. A sample was concentrated and was found to contain 92% of bromooctanol in addition to 1.9% of dibromooctane and 2.0% unconverted octanediol. After removal of the toluene by distillation in the reaction kettle and a Sambay distillation of the remaining residue, the yield was 254 kg (76%).

EXAMPLE 2

Preparation of 6-chlorohexan-1-ol

A 250 l kettle was charged with 14.16 kg of hexane-1,6-diol, followed by 150 l of toluene and 30 l of aqueous 36% strength HCl. The mixture was refluxed for 6 hours. The workup was carried out as described in Example 1, the purification being performed by distillation (boiling point 83° C./3 mbar). The yield was 13.3 kg (82%) of 6-chlorohexan-1-ol.

We claim:

1. A process for preparing a haloalcohol of the formula $$Hal-X-OH \qquad (I)$$

where X is straight-chain or branched, substituted or unsubstituted alkylene of 4 or 12 carbon atoms in the chain, which optionally are interrupted by one or more heteroatoms selected from the group consisting of oxygen and sulfur, and Hal is halogen which comprises reacting a diol of the formula $$HO-X-OH \qquad (II)$$

where X has the above meaning, with an aqueous hydrogen halide solution in a water-immiscible organic solvent which is inert under the reaction conditions and which is selected from the group consisting of aromatic and haloaromatic hydrocarbons, at from 90° to 150° C., using an excess of hydrogen halide, based on the diol of the formula II, of from 10 to 200 mole percent and setting a volume ratio of inorganic phase:organic phase of from 1:5 to 1:50, the reaction being carried out with thorough mixing to selectively produce the haloalcohol I without a continuous phase separation, either by extractive separation or by distillative separation, for removal of any components of the reaction system.

2. A process as claimed in claim 1, wherein aqueous hydrogen chloride or hydrogen bromide solution is used.

3. A process as claimed in claim 1, wherein a straight-chain diprimary $C_4-C_{12}$-diol is used.

4. A process as claimed in claim 1 wherein the excess of hydrogen halide, based on the diol of the formula II is from 20 to 50 mole percent.

5. A process as claimed in claim 1 wherein an aqueous hydrogen chloride solution is used with a concentration of 18 to 36% by weight.

6. A process as claimed in claim 1 wherein an aqueous hydrogen bromide solution is used with a concentration of 24 to 48% by weight.

7. A process as claimed in claim 1 wherein the volume ratio of inorganic phase:organic phase is set at from 1:5 to 1:15.

8. A process as claimed in claim 1 carried out at a temperature of from 90° to 120° C.

9. A process as claimed in claim 1 wherein the diol of formula II is selected from the group consisting of 1,4-butanediol, 1,5-pentanediol, 1,6-hexanediol, 1,7-heptanediol, 1,8-octanediol, 1,9-nonanediol, 1,10-decanediol, 1,11-undecanediol and 1,12-dodecanediol.

10. A process as claimed in claim 1 wherein the inert organic solvent used is selected from the group consisting of benzene, toluene, xylene, monochlorobenzene and dichlorobenzene.

* * * * *

UNITED STATES PATENT AND TRADEMARK OFFICE
CERTIFICATE OF CORRECTION

PATENT NO. : 5,237,113
DATED : August 17, 1993
INVENTOR(S) : Becker et al.

It is certified that error appears in the above-indentified patent and that said Letters Patent is hereby corrected as shown below:

On the title page, insert the following information:
   --[30]  Oct. 4, 1936 (DE) Fed. Rep. of Germany  3633886--

Column 4, line 20, change "or" to --to--.

Signed and Sealed this

Nineteenth Day of April, 1994

Attest:

BRUCE LEHMAN

Attesting Officer

Commissioner of Patents and Trademarks